United States Patent [19]

Frazer

[11] Patent Number: Plant 6,858

[45] Date of Patent: Jun. 13, 1989

[54] DIEFFENBACHIA HYBRIDA HILO

[75] Inventor: Edwin J. Frazer, Brisbane, Australia

[73] Assignee: Hartman Plant Laboratories, Inc., Santa Paula, Calif.

[21] Appl. No.: 23,607

[22] Filed: Mar. 9, 1987

[51] Int. Cl.[4] ..... A01H 5/00

[52] U.S. Cl. ..... Plt./88

[58] Field of Search ..... Plt./88

*Primary Examiner*—Robert E. Bagwill
*Attorney, Agent, or Firm*—Hale and Dorr

[57] ABSTRACT

A new and distinct cultivar of Dieffenbachia known as Dieffenbachia Hybrida Hilo, which is a seedling cross between Wilson's Delight and Key West.

1 Drawing Sheet

The invention comprises a new and distinct cultivar of Dieffenbachia known as Dieffenbachia Hybrida Hilo.

The new cultivar is a product of a seedling cross between Dieffenbachia Wilson's Delight and Key West.

The following observations, measurements and values describe plants grown in Alva, Fla. under greenhouse conditions that closely approximate those generally used in horticultural practice. All color references are measured against The Royal Horticultural Society Colour Chart. Colors are approximate as color depends on horticultural practices such as light level and fertilization rate among others.

The following traits have been repeatedly observed to be characteristics which in combination distinguish Dieffenbachia Hilo from other commercially available Dieffenbachia.

DISTINCTIONS

1. Long narrow leaves that lie horizontal, breaking the rounded outline of the central plant.
2. Numerous breaks with white midveins gives color and fullness from the apex to the pot surface.
3. Leaves are patterned and colored on both sides and are positioned such that any leaf you can see is patterned.
4. The petiole midrib is lighter than the stem.
5. The combination of white veins and midribs and numerous breaks with color make the plant extremely colorful from the apex to the pot surface.
6. The first break is almost as tall as the main stem making the plant appear wide and full at the apex.
7. The midrib is flexible enough to touch the tip of the leaf to its base without damage.

The appearance and distinctive character of Hilo is shown in the FIGURE which is a true color photograph of the cultivar in an eight-inch pot.

DESCRIPTION

Propagation: Asexual production either through tissue culture or division.

Plant: In a 6 inch pot, Hilo will be approximately 20 cm to 28 cm from the soil surface to the junction of the petioles of the last two unrolled leaves and approximately 65 cm to 75 cm in width after approximately 26 weeks to 36 weeks under appropriate growing conditions from tissue culture. All measurements are based on the above parameters.

Stem:

*Growth pattern.*—The stem is erect in growth and will be approximately 2.0 cm to 2.5 cm in diameter at a height of 5 cm above the soil surface. Internode distance will be approximately 1.4 cm to 1.8 cm at a height of 3 cm above the soil.

*Color.*—The stem is dark green with no pattern. (139A).

Petiole (based on the third expanded leaf from apex of the main shoot):

*Pattern.*—The petiole has fleshy edges extending from the midrib that will be referred to as wings. The wings will be approximately 7 mm to 11 mm wide 1 cm below the leaf base. The wings extend from the base of the petiole to the leaf base on large new leaves. On smaller leaves this distance may be as much as 4.5 cm. The apex of the wings is emarginate. The petiole follows the stem axis but diverges from the axis approximately 4.5 cm to 5.0 cm from the leaf base forming a horizontal distance from the edge of the stem to the leaf base of approximately 2.3 cm to 3.0 cm.

*Physical dimensions.*—The petiole will be approximately 12 cm to 13 cm from its base to the base of the leaf. The petiole will be approximately 6 mm to 8 mm in diameter one-half way between the top of the wing to the bottom of the leaf.

*Color and color pattern.*—The petiole wings will be green and light green faint blotches and the midrib will be light green (2D, 4D).

Leaf:

*Growth pattern.*—The leaf will be ovate with an acuminate apex and an obtuse/cordate base. The margin is entire. The leaf is asymmetric with the side of the leaf unrolling first having less surface area and less undulations on the leaf margin than the side unrolling last. The leaf is oriented 10° to the stem axis at the time of full unrolling changing to 100° to the stem axis as more leaves unroll above it. The midrib droops slightly over the length of the leaf. The leaf blade is flat from the midrib to the margin.

*Physical dimensions.*—For the potsize and growing time indicated, the largest leaf will be approximately 37 cm to 41 cm long and approximately 15 cm to 17 cm wide. An average sized leaf will be approximately 27 cm to 29 cm long and approximately 11 cm to 13 cm wide. The leaf thickness is medium.

*Midrib.*—The midrib is thick and slightly green at the leaf base fading quickly to ivory (2D,149D).

*Primary veins.*—The primary veins are sunken into the adaxial side and protruding out of the abaxial side.

*Color and pattern.*—The adaxial surface of both the mature, older leaf and the newly-opened leaf has a midrib color of 136B, 137A at the basipetal portion, changing to 2D, 149D toward the apex of the leaf and a leaf blade color of 155B, 137A. The abaxial surface of the mature, older leaf and the newly-opened leaf has a midrib color of 2D to 4D and a leaf blade color of 191A.

Axillary breaks: There will be approximately 7 to 9 axillary breaks with at least 1 leaf expanded. Leaves will show color by the first leaf and will have true color and pattern by the third leaf.

Inflorescences: Not present.

Roots: Thick white roots with finer laterals.

General observations: Dieffenbachia Hilo is similar in leaf pattern to Wilson's Delight but has narrower leaves. The symmetry of the plant is interrupted by leaves jutting out from the center of the plant. The large number of breaks and the size of the first break give the plant a full appearance. The early color on the new breaks, the visibility of the pattern on both sides of the leaf and the petiole midrib give the plant attractive contrast.

I claim:

1. A new and distinct cultivar of Dieffenbachia as described and illustrated.

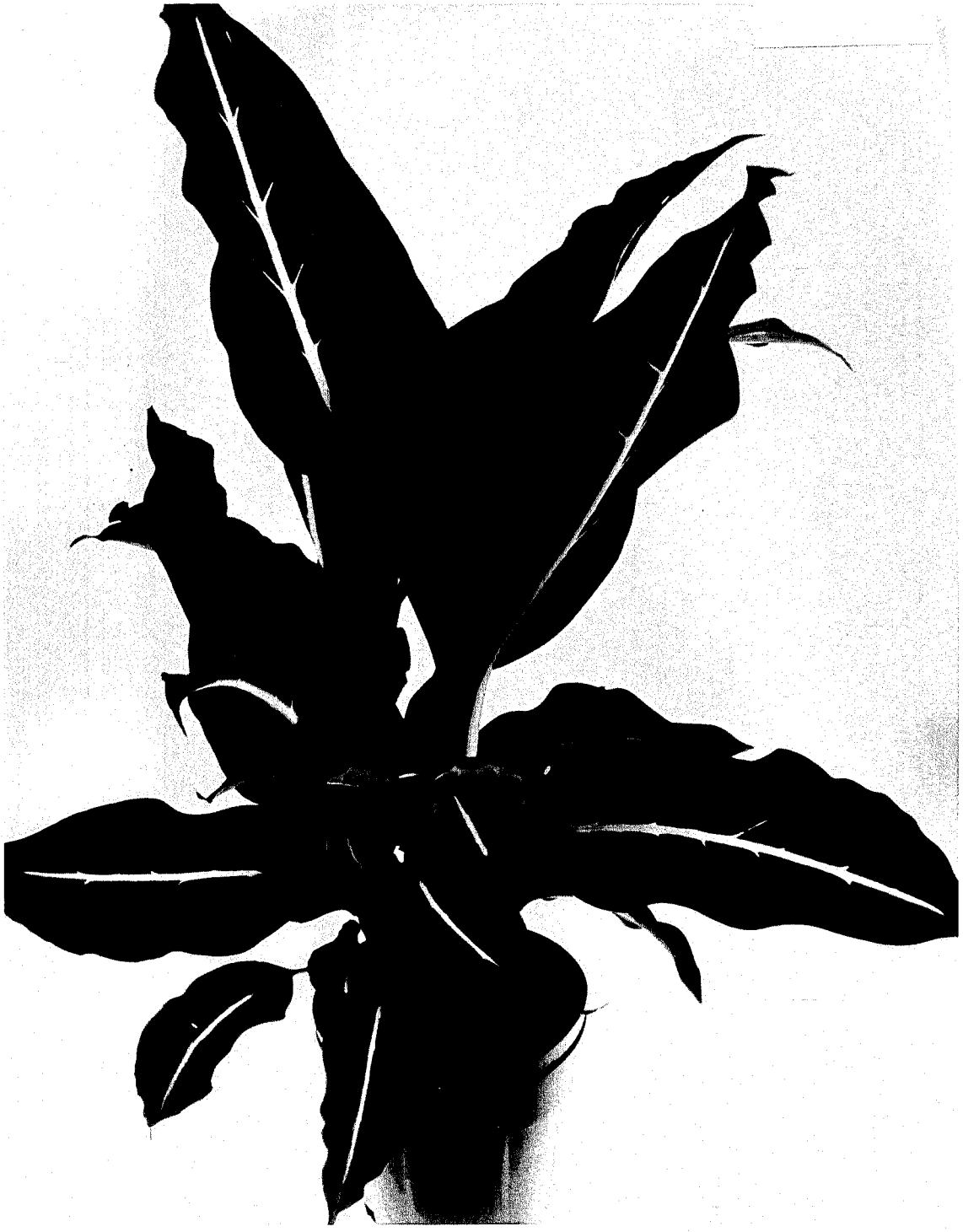

* * * * *